(12) United States Patent
Toth

(10) Patent No.: US 7,391,843 B2
(45) Date of Patent: Jun. 24, 2008

(54) SYSTEMS AND METHODS FOR ADJUSTING NOISE IN A MEDICAL IMAGING SYSTEM

(75) Inventor: Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 416 days.

(21) Appl. No.: 11/156,886

(22) Filed: Jun. 20, 2005

(65) Prior Publication Data

US 2006/0285634 A1 Dec. 21, 2006

(51) Int. Cl.
*A61B 6/03* (2006.01)

(52) U.S. Cl. .............................. 378/16; 378/4

(58) Field of Classification Search ................ 378/4, 378/8, 16
See application file for complete search history.

(56) References Cited

U.S. PATENT DOCUMENTS

| | | | |
|---|---|---|---|
| 3,755,672 A * | 8/1973 | Edholm et al. .............. 378/158 |
| 4,423,893 A | 1/1984 | Holmes | |
| 5,782,078 A | 7/1998 | Brantley | |
| 6,131,850 A | 10/2000 | Hey et al. | |
| 6,330,985 B1 | 12/2001 | Manteiga et al. | |
| 6,537,220 B1 | 3/2003 | Friemel et al. | |
| 6,614,873 B1 * | 9/2003 | Taylor et al. .................. 378/62 |
| 6,659,878 B2 | 12/2003 | Anderson | |
| 2005/0031082 A1 * | 2/2005 | Haaga et al. ................. 378/108 |

OTHER PUBLICATIONS

Kalra et al., "Sixteen-Detector Row CT of Abdomen and Pelvis: Study for Optimization of Z-Axis Modulation Technique Performed in 153 Patients", Radiology 2004, Oct. 2004, vol. 233, Issue 1, pp. 241-249.*
U.S. Appl. No. 09/683,128, filed Nov. 21, 2001, Thomas Toth et al.
U.S. Appl. No. 10/765,582, filed Jan. 27, 2004, Thomas Toth et al.
U.S. Appl. No. 10/605,789, filed Oct. 27, 2003, Thomas Toth et al.
U.S. Appl. No. 10/765,583, filed Jan. 27, 2004, Thomas Toth et al.
U.S. Appl. No. 10/765,617, filed Jan. 27, 2004, Thomas Toth et al.
U.S. Appl. No. 10/765,618, filed Jan. 27, 2004, Thomas Toth et al.

* cited by examiner

*Primary Examiner*—Chih-Cheng G Kao
(74) *Attorney, Agent, or Firm*—Armstrong Teasdale LLP

(57) ABSTRACT

A method for adjusting noise in an imaging system is described. The method includes adjusting, by a processor, a noise within an image based on a patient size.

16 Claims, 6 Drawing Sheets

SYSTEMS AND METHODS FOR ADJUSTING NOISE IN A MEDICAL IMAGING SYSTEM

BACKGROUND OF THE INVENTION

This invention relates generally to medical imaging systems and methods and more particularly to system and methods for adjusting noise in the medical imaging systems.

Typically, in computed tomography (CT) imaging systems, a gantry includes an X-ray source that emits a fan-shaped beam toward an object, such as a patient. The beam, after being attenuated by the patient, impinges upon an array of radiation detectors. The intensity of the attenuated beam radiation received at the detector array is typically dependent upon the attenuation of the X-ray beam by the patient. Each detector element of the detector array produces a separate electrical signal indicative of the attenuated beam received by each detector element. The electrical signals are transmitted to a data processing unit for analysis which ultimately results in a formation of an image.

Generally, the X-ray source and the detector array are rotated with a gantry within an imaging plane and around the patient. X-ray sources typically include X-ray tubes, which conduct a tube current and emit the X-ray beam at a focal point. X-ray detectors typically include a collimator for collimating X-ray beams received at the detector, a scintillator for converting X-rays to light energy adjacent the collimator, and photodiodes for receiving the light energy from the adjacent scintillator.

The CT imaging systems use a projection area or projection data from a scan acquisition, such as a scout scan, to determine a tube current per rotation of the gantry that maintains a constant noise independent of patient sizes of a first, second, and a third patient. For example, a CT scanner manufactured by a manufacturer A provides a first constant noise and a first tube current independent of the patient sizes scanned by the scanner. Another CT scanner manufactured by a manufacturer B provides a second constant noise and a second tube current independent of the patient sizes scanned by the scanner. However, if the CT imaging systems scan the second patient that may be larger than the first patient by applying the same amount of tube current as that applied to the first patient, quality of images of the second patient is degraded by image noise. On the other hand, if the CT imaging systems scan the third patient that may be smaller than the first patient by applying the same amount of tube current as that applied to the first patient, quality of images of the third patient may not be degraded but the third patient may be exposed to a higher x-ray dose than necessary.

BRIEF DESCRIPTION OF THE INVENTION

In one aspect, a method for adjusting noise in an imaging system is described. The method includes adjusting, by a processor, a noise within an image based on a patient size.

In another aspect, a medical imaging system is described. The medical imaging system includes a source configured to generated radiation incident upon a patient, a detector configured to detect the radiation, and a processor configured to adjust a noise within an image based on a patient size of the patient.

In yet another aspect, a computer configured to adjust a noise within an image based on a patient size is described.

DETAILED DESCRIPTION OF THE INVENTION

Figure 1:
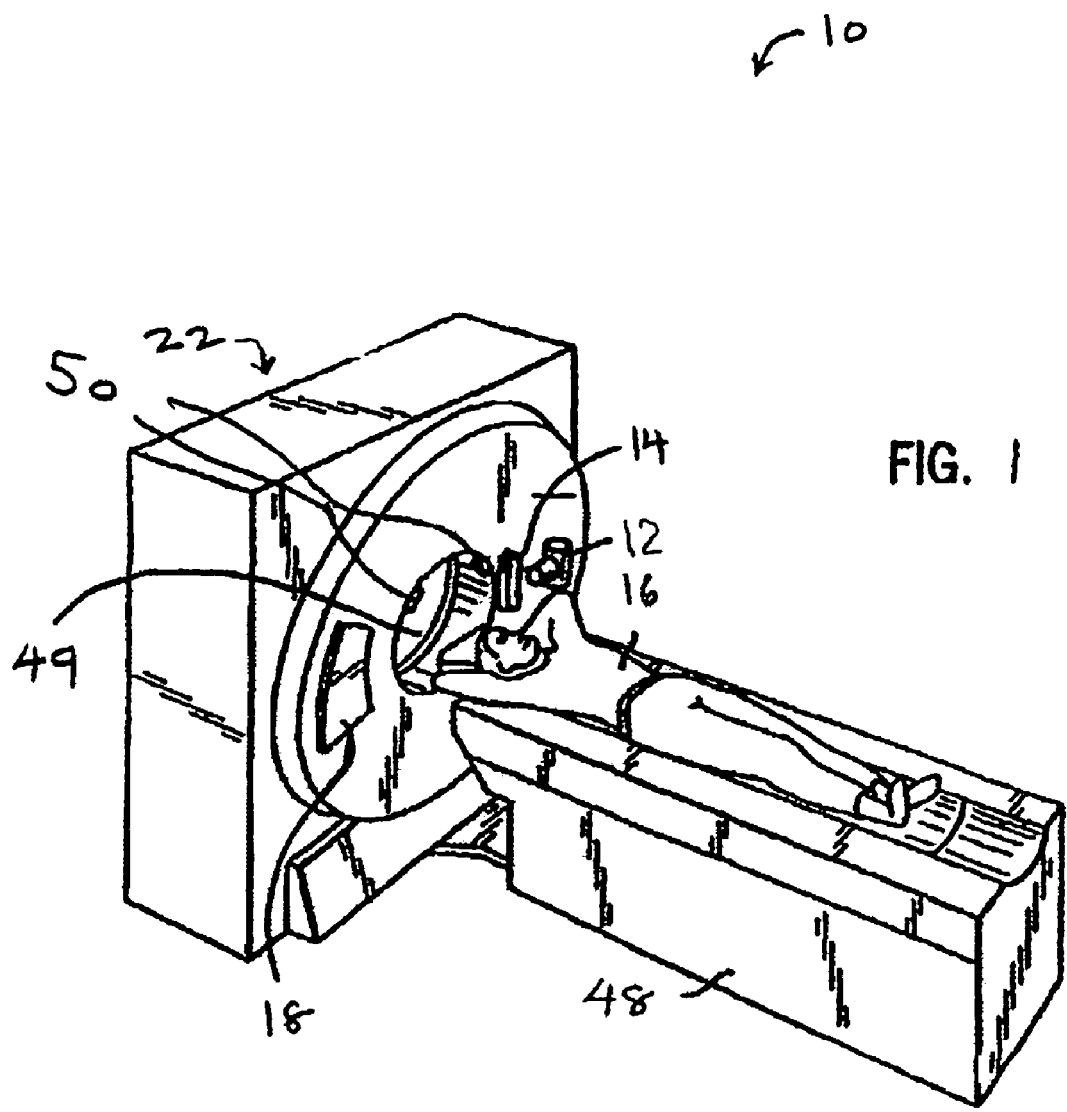
FIG. 1 is an isometric view of an embodiment of a computed tomography system in which a method for adjusting noise is implemented.
Figure 2:
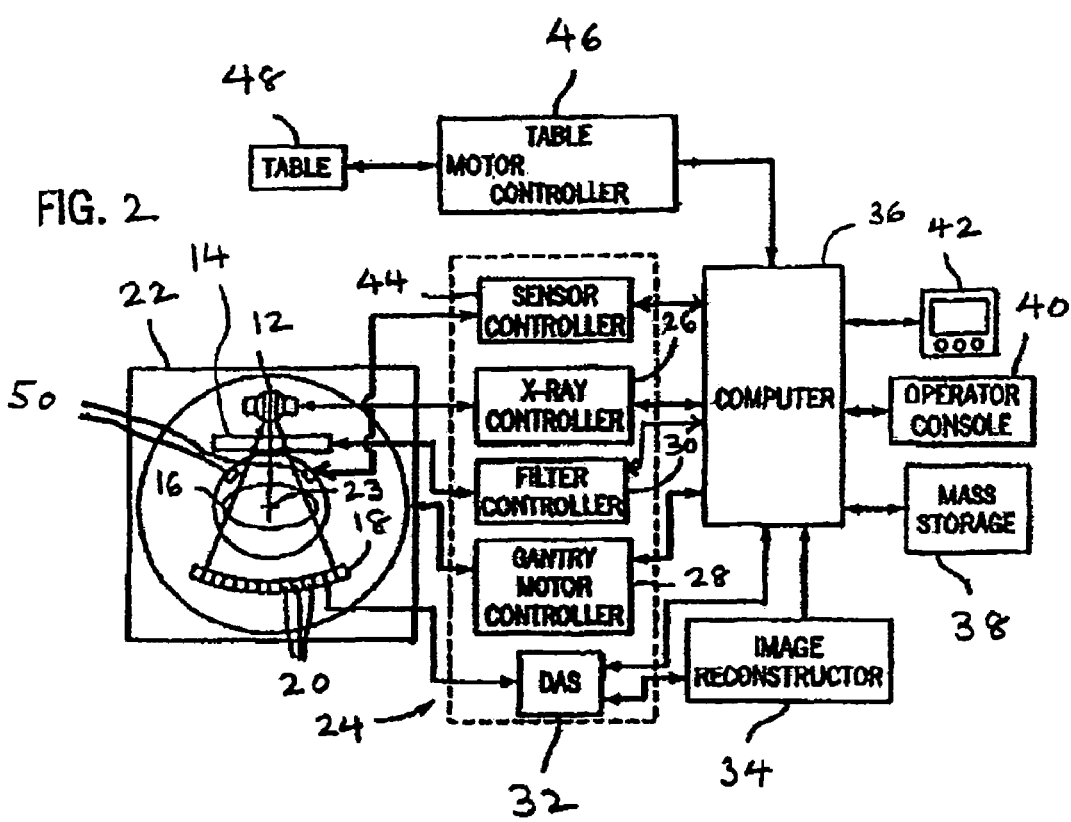
FIG. 2 is a block diagram of an embodiment of the computer tomography system of FIG. 1.

Referring to FIGS. 1 and 2, a computed tomography (CT) imaging system 10 is shown as including a gantry 22. CT system 10 is a "third generation" CT system. In an alternative embodiment, CT system 10 may be an energy integrating, a photon counting (PC), or a photon energy discriminating (ED) CT detector system. Gantry 22 has an x-ray source 12 that projects a beam of x-rays through a filter 14 toward a detector array 18. Filter 14 filters x-rays from x-ray source 12 to generate filtered x-rays. The filtered x-rays pass through an object 16, such as a patient, to generate attenuated x-rays. Detector array 18 is formed by a plurality of detectors 110 which together sense the attenuated x-rays. In an alternative embodiment, each detector 20 of detector array 18 may be a photon energy integrating detector, a photon counting, or a photon energy discriminating detector. Each detector 20 produces an electrical signal that represents an intensity of the attenuated x-rays. During a scan to acquire x-ray projection data, gantry 22 and components mounted on gantry 22 rotate about a center of rotation 23.

Rotation of a gantry 22 and an operation of x-ray source 12 are governed by a control mechanism 24 of CT system 10. Control mechanism 24 includes an x-ray controller 26 that provides power and timing signals to x-ray source 12, a gantry motor controller 28 that controls a rotational speed and position of gantry 22, and a filter controller 30 that controls filter 14. A data acquisition system (DAS) 32 in control mechanism 24 samples and digitizes projection data from detectors 20 and converts the projection data to sampled and digitized projection data for subsequent processing. An image reconstructor 34 receives the sampled and digitized projection data from DAS 32 and performs image reconstruction, such as, filtered backprojection, to generate a reconstructed image. The reconstructed image is applied as an input to a computer 36 which stores the reconstructed image in a mass storage device 38. X-ray controller 26 adjusts a tube current within x-ray source 12 based on a quality of the reconstructed image.

Computer 36 also receives commands and scanning parameters from an operator via a console 40 that has a user interface device. A cathode ray tube display 42 allows a user, such as an operator, to observe the reconstructed image and other data from computer 36. The commands and scanning parameters are used by computer 36 to provide control signals and information to DAS 32, x-ray controller 26, a sensor controller 44, filter controller 30, and gantry motor controller 28. In addition, computer 36 operates a table motor controller 46 which controls a motorized table 48 to position object 16 within gantry 22. Particularly, table motor controller 46 adjusts table 48 to move portions of object 16 and center object 16 in a gantry opening 49 (shown in FIG. 1). Sensors 50 are positioned within gantry opening 49 to collect patient position and contour data. An example of the patient position and contour data includes a location or a point, on object 16, scanned along a z-axis that is parallel to a height of object 16. Sensors 50 are connected to sensor controller 44 that controls an operation of sensors 50. Sensor controller 44 receives the patient position and contour data from sensors 50 and provides the patient position and contour data to computer 36 to be processed.

In an alternative embodiment, a high frequency electromagnetic energy projection source configured to project high frequency electromagnetic energy toward object 16 may be used instead of x-ray source 12. A detector array disposed within a gantry and configured to detect the high frequency electromagnetic energy may also be used instead of detector array 18.

Figure 3:
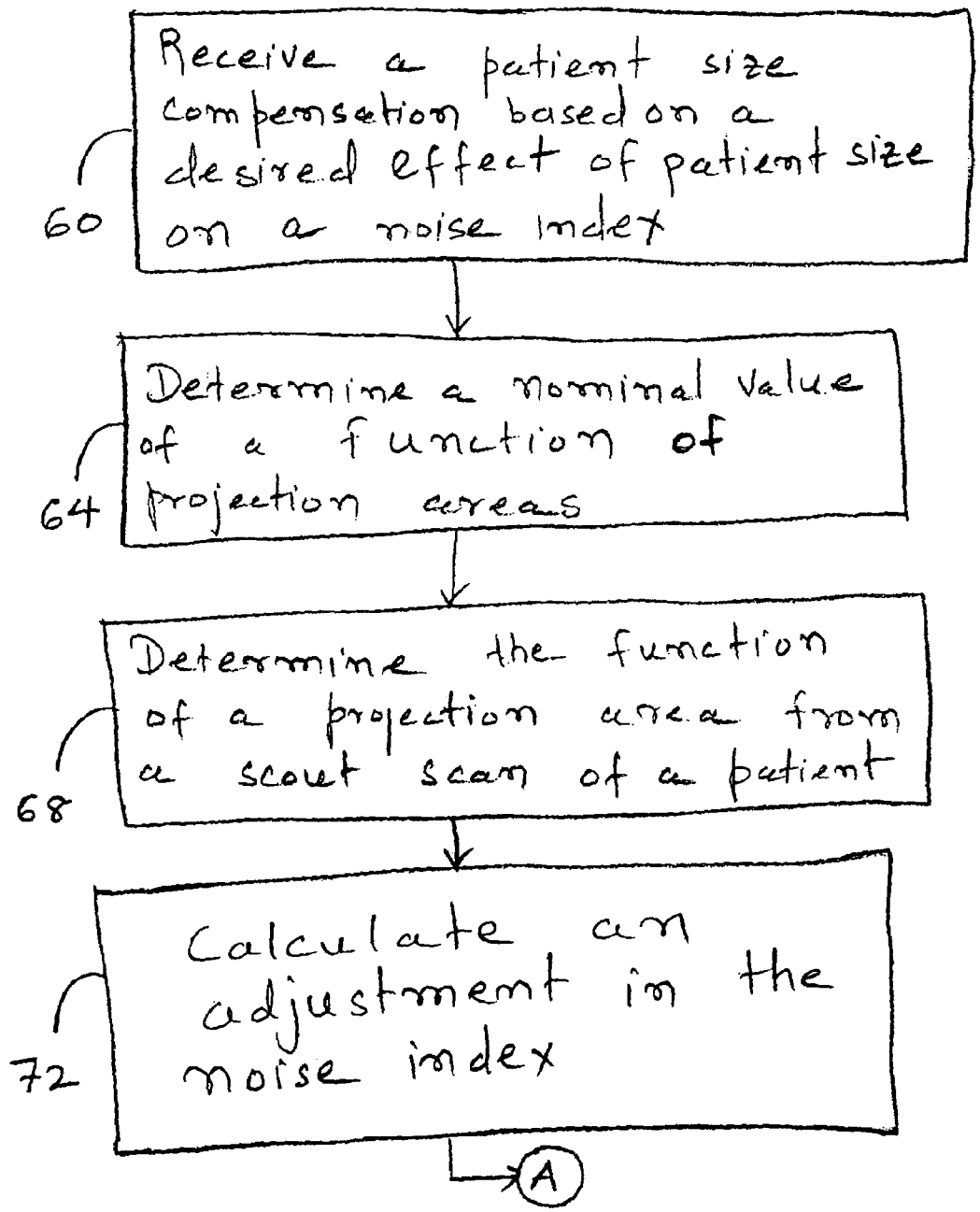
FIG. 3 is a flowchart of an embodiment of the method for adjusting noise.
Figure 4:
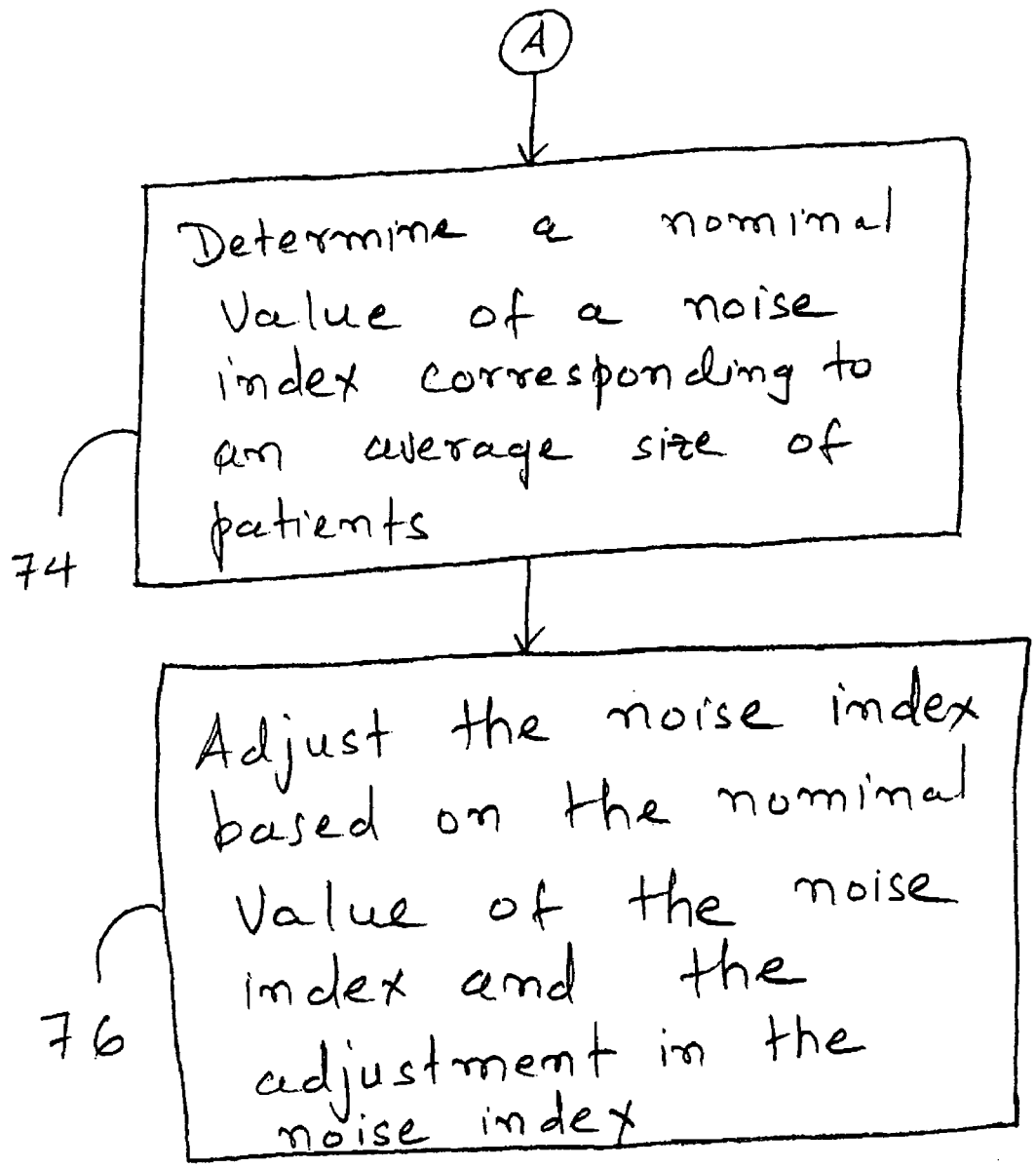
FIG. 4 is a continuation of the flowchart of FIG. 3.

FIGS. 3 and 4 are a flowchart of an embodiment of a method for adjusting noise in a medical imaging system, such as CT system 10. The method for adjusting noise can be executed by any or a combination of computer 36, x-ray controller 26, filter controller 30, sensor controller 44, gantry motor controller 28, and table motor controller 46.

Computer 36 receives 60, as an input, a patient size compensation from the user. The patient size compensation is based on an effect, desired by the user, of a size of object 16 on a noise index. A noise index is a desired standard deviation or noise in an image to be reconstructed. Example of the patient size compensation include a range from and including 'none' to 'full'. As another example, a range of the patient size compensation can include discrete values, such as, 0, 0.5, and 1, of the patient size compensation. As yet another example, the range of the patient size compensation can include continuous values, such as, 0, 0.1, 0.2, and 0.3, of the patient size compensation.

When the user selects 'none' on console 40, a noise index does not change with a change in a size of object 16. Upon selecting 'none', x-ray controller 26 adjusts a tube current of x-ray source 12 for a constant value of a noise index. When the user selects 'full' on console 40, there is a maximum amount of change in a noise index with a change m in a size of object 16. When the user selects the patient size compensation between 'none' and 'full', there is a change less than the maximum amount in a noise index with the change m in a size of object 16.

Figure 5:
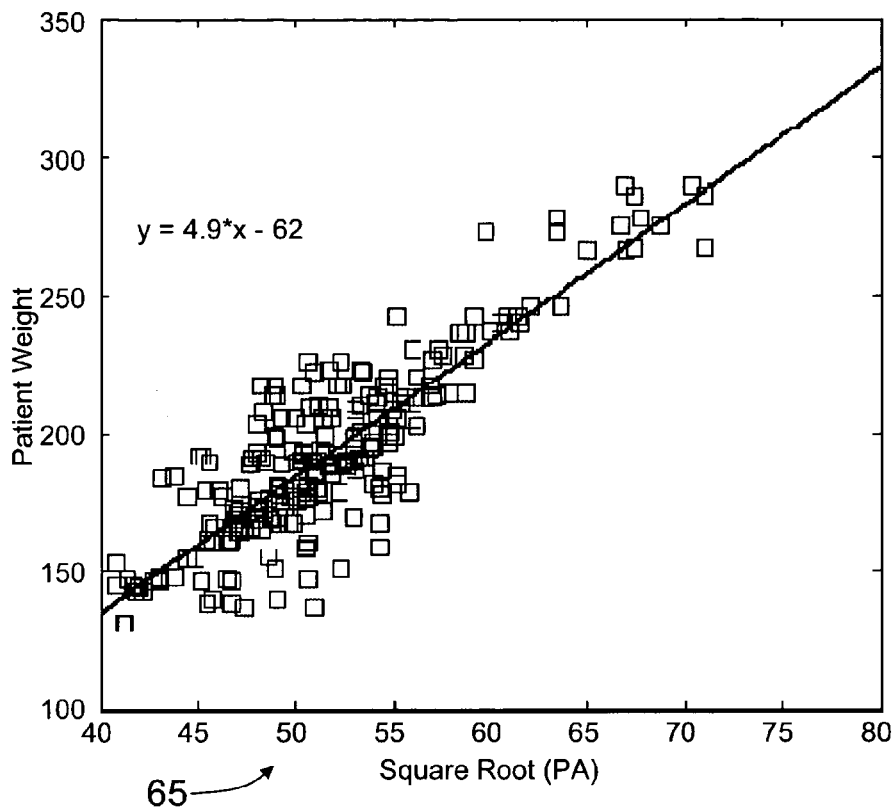
FIG. 5 shows graphs representing exemplary relationships between patient sizes of a plurality of patients and a function of projection areas obtained by scanning the patients with the computed tomography system of FIG. 1.
Figure 5:
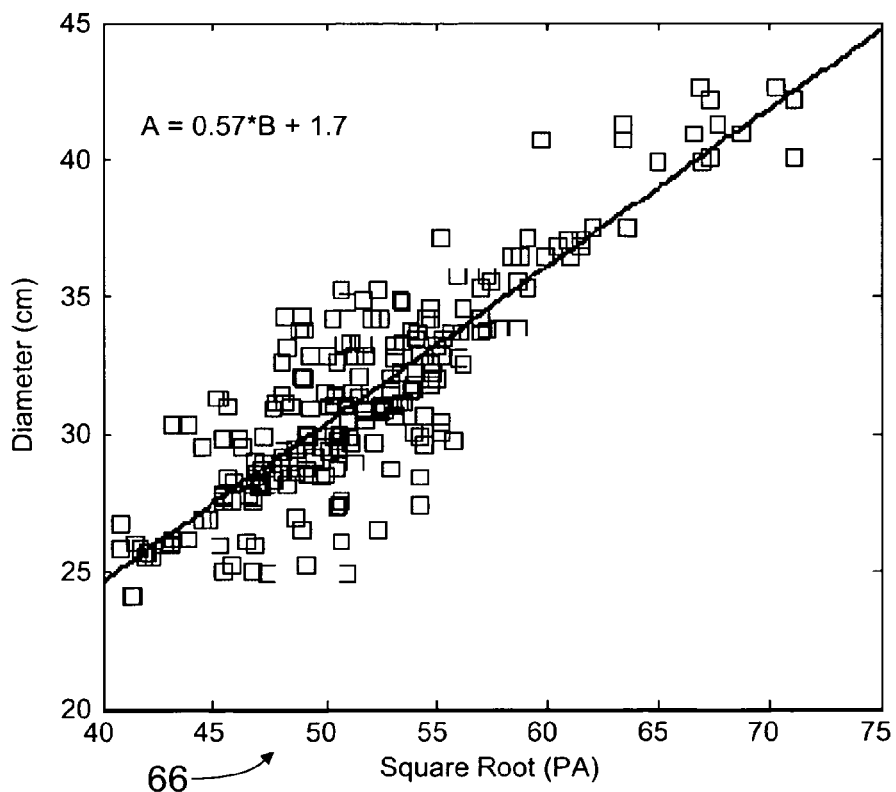

Computer 36 determines 64 a nominal value of a function, such as a square root, of a projection area as follows. A plurality of parts, such as a head or body or neck, of a plurality of patients are scanned by CT system 10. Computer 36 computes a plurality of projection areas from the sampled and digitized data. Computer 36 calculates a projection area by integrating the sampled and digitized data within a projection generated from detector array 18 when x-ray source 12 is at a fixed position and detector array 18 is at a fixed position. The same type of part, such as a head, neck, or body, of a plurality of patients is scanned to compute a plurality of projection areas. Computer 36 plots patient sizes, such as weights and diameters, of a plurality of patients versus the function of each of a plurality of projection areas obtained by scanning the patients. The patient sizes are input into computer 36 via console 40. In an alternative embodiment, computer 36 calculates the patient sizes from other data input via console 40. For example, computer 36 calculates diameters of a plurality of patients by applying d = average(PM/μ), where d is a diameter of a patient, PM is the sampled and digitized projection data, μ is a patient density assumption input via console 40, and average is an average function. Examples of μ range from 0.14 to 0.24 for typical human soft tissue. Examples of the plots are shown in FIG. 5. FIG. 5 shows a graph 65 of weights of a plurality of patients plotted on a y-axis versus the function of each of a plurality of projection areas plotted on an x-axis. A plurality of projection areas shown in FIG. 5 are obtained by scanning abdomens of a plurality of patients. Graph 65 is represented by Y=4.9X—62, where Y is a weight of a patient and X is a square root of a projection area obtained by scanning the patient. A graph 66 shows diameters of a plurality of patients plotted on a y-axis versus the function of each of a plurality of projection areas plotted on an x-axis. Graph 66 is represented by A =0.57B+1.7, where A is a diameter of an abdomen of a patient and B is a square root of a projection area obtained by scanning the patient. In an alternative embodiment, computer 36 may not generate the plots. Computer 36 calculates an average value of a plurality of patient sizes of a plurality of patients and obtains a nominal value of the function from the average value. As an example, computer 36 determines a nominal value of the function corresponding to an average value of patient sizes shown in the plots. As an example, a nominal value of the function is 28.4 and is obtained by scanning heads of a plurality of patients. Another example of a nominal value of the function is 48.2 and is obtained by scanning bodies of a plurality of patients.

Referring back to FIGS. 3 and 4, computer 36 determines 68 the function of a projection area from a scout scan of object 16. CT system 10 performs a scout scan of object 16 to obtain the sampled and digitized projection data. Computer 36 calculates a projection area by integrating the sampled and digitized data within a projection generated from detector array 18 when x-ray source 12 is at a fixed position and detector array 18 is at a fixed position. Computer 36 computes the function of a projection area generated from a scout scan.

Computer 36 calculates 72 an adjustment in a noise index by executing a linear equation represented as $$\Delta NF = [\{f(PA)_{scout} - f(PA)_{nominal}\} PSC]a \qquad (1)$$

where f is the function of a projection area, $(PA)_{scout}$ is a projection area obtained from a scout scan at a specific location of the z-axis along a height of object 16, $(PA)_{nominal}$ is a nominal value of the function of each of a plurality of projection areas obtained by scanning a plurality of patients at the location, a is a constant, such as, for example, 0.0333 or 1, and PSC is the patient size compensation. In an alternative embodiment, computer 36 restricts a range of $\Delta NF$ of equation (1) between a maximum value and, such as, for example, 0.8, and a minimum value, such as, for example, −0.8.

Figure 6:
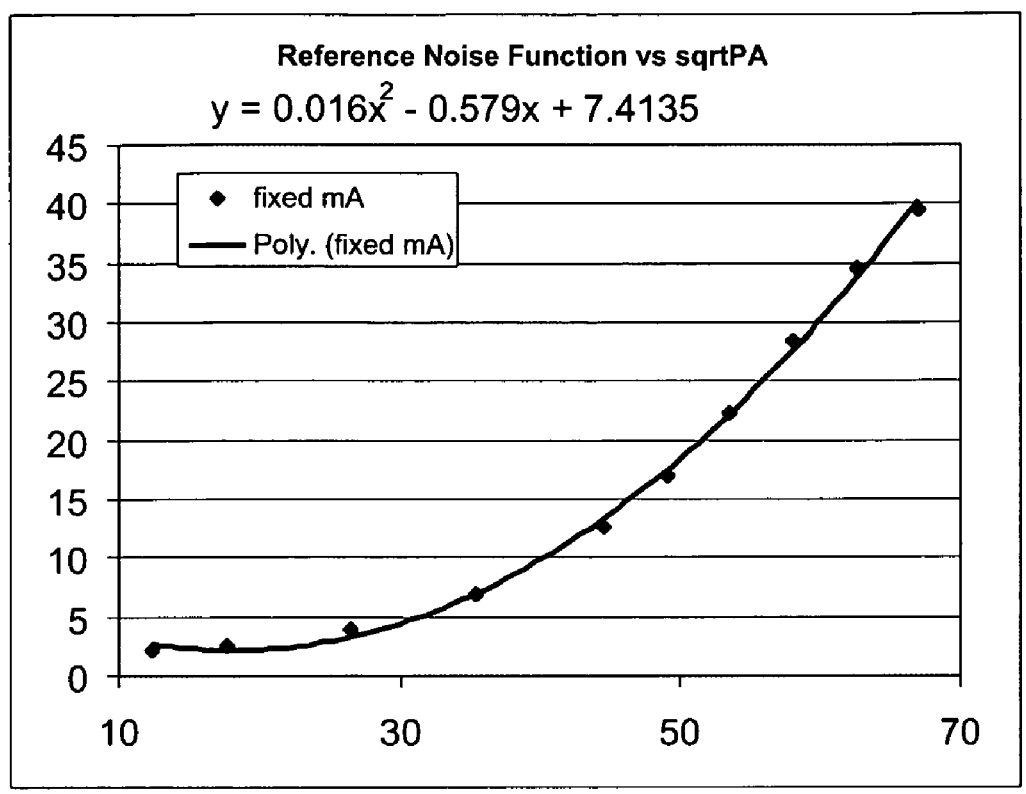
FIG. 6 shows a graph representing an exemplary relationship between an adjustment in a noise index and the function of a projection area.

In another alternative embodiment, computer 36 calculates 72 an adjustment in a noise index by applying a non-linear equation represented as $$N(x) = px^2 - qx + r, \text{ if } x > s \qquad (2)$$
$$= t, \text{ if } x \leq s$$

where x is the function of a projection area. An example of p is 0.016, q is 0.579, r is 7.4135, s is 17.68, and t is 2.607. An example of a plot of N(x) is shown in FIG. 6. In FIG. 6, y represents N(x), which is plotted along a y-axis and x of equation (2) is plotted along an x-axis. In yet another alternative embodiment, computer 36 restricts N(x) as being asymptotic to both a maximum value and a minimum value.

In still another alternative embodiment, computer 36 calculates an adjustment in a noise index by executing a higher-order equation than equation (2).

Referring back to FIGS. 3 and 4, computer 36 determines 74 a nominal value of a noise index. A nominal value of a noise index is calculated from an average size of a plurality of patients. For example, clinical studies that establish a relationship between noise indexes in images obtained by scanning abdomens of a plurality of patients and weights of the patients are stored in mass storage device 38 accessible by computer 36. The clinical studies show a noise index of 10 for weights of patients less than 120 pounds, a noise index of 15 for weights of patients greater than 200 lbs, and a noise index of 12.5 for weights of patients between 120 pounds and 200 pounds. Computer 36 averages weights of a plurality of patients from the clinical studies to generate an average weight and obtains from the clinical studies a nominal value of a noise index corresponding to the average weight. For example, upon determining that an average weight of a plurality of patients is 160 pounds, computer 36 determines a nominal value of a noise index to be 12.5 from the clinical studies.

Computer 36 adjusts 76 a noise index based on a nominal value of the noise index and an adjustment, such as ΔNF, of the noise index. As an example, computer 36 adjusts a noise index by executing an equation represented as $$PNI=NI(1+\Delta NF) \quad (3)$$

where PNI is an adjusted value of a noise index at a particular location along the z-axis at which ΔNF is calculated, and NI is a nominal value of the noise index at the particular location. In an alternative embodiment, computer 36 calculates a plurality of adjusted values PNIs of noise indexes at different locations along the z-axis and averages the adjusted values to generate a mean adjusted noise index.

In an alternative embodiment, computer 36 calculates 72 an adjustment in a noise index by using a nominal value of the function of each of a plurality of projection areas obtained from a scout scan of object 16 over different locations along the z-axis. As an example, computer 36 calculates an adjustment in the noise index by executing an equation represented as $$N(x_{nominal}) = p(x_{nominal})^2 - qx_{nominal} + r, \text{ if } x_{nominal} > s \quad (4)$$
$$= t, \text{ if } x_{nominal} \leq s$$

where $x_{nominal}$ is an average of the function of each of a plurality of projection areas obtained from a scout scan of object 16 over different locations along the z-axis.

In yet another alternative embodiment, computer 36 adjusts 76 a noise index by applying an equation represented as $$PNI(x)=NI[1+\{(N(x)/N(x_{nominal}))-1\}PSC] \quad (5)$$

Computer 36 calculates multiple values of adjustments in a noise index by applying at least one of equations (1), (2), (3), (4), and (5) to a plurality of patients having a plurality of projection areas and generates a table of the noise indexes with the projection areas. For example, an adjustment 1 in a noise index is obtained by applying at least one of equations (1), (2), (3), (4), and (5) to a patient 1 having a projection area 1, and an adjustment 2 in a noise index is obtained by applying at least one of equations (1), (2), (3), (4), and (5) to a patient 2 having a projection area 2. Each adjustment in a noise index corresponds to a value of a potential, such as a kilovolt peak (kVp) potential, applied to x-ray source 12 and the potential is also stored in the table. For example, x-ray source 12 applies a kVp1 for the adjustment 1 in a noise index and applies a kVp2 for the adjustment 2 in a noise index.

X-ray controller 26 determines, from the table and a projection area of a patient obtained from a scout scan, a potential to be applied in scanning the patient. For example, if the projection area 1 is obtained from a scout scan of a patient 3 different from the patient 1, x-ray controller 26 obtains the kVp1 from the table and the kVp1 corresponds to the projection area 1. X-ray source 12 applies kVp1 to the patient 3 when a scan of the patient 3 is conducted by CT system 10.

Moreover, mass storage device 38 stores a filter parameter, such as a thickness or material, of filter 14 corresponding to a potential applied when using the filter parameter. For example, mass storage device 38 stores a filter parameter 1 that is used when the kVp1 is applied to the patient 1. A scout scan of a patient is performed to obtain a projection area of the patient. For example, CT system 10 performs a scout scan to obtain the projection area 1 of the patient 3. Filter controller 30 determines a filter parameter from the table and from the function of a projection area obtained from a scout scan. As an example, filter controller 30 determines the filter parameter 1 upon determining from a scout scan that the patient 3 has the projection area 1. The patient 3 is then scanned by applying the filter parameter 1.

In an alternative embodiment, a combination of a filter parameter and a potential determined from the table is used to scan a patient having a projection area determined from a scout scan of the patient. For example, x-ray controller 26 applies the kVp1 and filter controller 30 applies the filter parameter 1 when x-ray controller 26 and filter controller 30 determine that the patient 3 has the projection area 1 from a scout scan of the patient 3.

A quality of an image is governed by attenuation of the filtered x-rays by object 16 and the attenuation is compensated for by transmitting a sufficient number of photons through object 16. A low potential increases a contrast of a human tissue and injected or alternatively ingested contrast agents. It is, therefore, desirable to use a lowest potential that provides sufficient penetration through object 16 while filtering out soft or low energy x-ray that have virtually no probability to penetrate object 16. CT system 10 is used to assess a patient size of object 16 and automatically determine a lowest potential and appropriate filtration. For example, when CT system 10 determines that the patient 3 has the projection area 1 and obtains kVp1 and a kVp3, where both kVp1 and kVp3 correspond to the projection area 1 and generate the same quality of an image, CT system 10 determines that kVp1 is lower than kVp3 and outputs kVp1 as a recommendation for applying to x-ray source 12.

As used herein, the term computer is not limited to just those integrated circuits referred to in the art as a computer, but broadly refers to a processor, a microcontroller, a microcomputer, a programmable logic controller, an application specific integrated circuit, and another programmable circuit, and these terms are used interchangeably herein. Moreover, as used herein, the term controller is not limited to just those integrated circuits referred to in the art as a controller, but broadly refers to a computer, a processor, a microcontroller, a microcomputer, a programmable logic controller, an application specific integrated circuit, and another programmable circuit, and these terms are used interchangeably herein.

It is noted that in an alternative embodiment, the sampled and digitized projection data is used instead of a projection area. For example, computer 36 determines a nominal value of the function of the sampled and digitized projection data instead of a nominal value of the function of a projection area.

Technical effects of systems and methods for adjusting noise include adjusting noise within an image to be reconstructed, where the adjustment is made based on a size of object 16. Other technical effects of the systems and methods include generating the table including a plurality of combinations of filter parameters and tube currents based on the function of a projection area of a patient to be scanned. Filter parameters and tube current are selected by computer 36 based on projection areas of a plurality of patients to be scanned.

While the invention has been described in terms of various specific embodiments, those skilled in the art will recognize that the invention can be practiced with modification within the spirit and scope of the claims.

What is claimed is:

1. A method comprising adjusting, by a processor, a noise index within an image based on a patient size and a desired effect of a change in the patient size on a change in the noise index.

2. A method in accordance with claim 1 further comprising adjusting parameters of a filter based on a projection area generated from a patient having the patient size.

3. A method in accordance with claim 1 further comprising:
receiving, from a user, the patient size as an input; and
outputting, by the processor, the noise index based on the patient size.

4. A method in accordance with claim 1 further comprising:
determining, by the processor, an average size of parts of a plurality of patients; and
determining, by the processor, a nominal value of a function of a projection area from the average size, wherein said adjusting a noise index comprises adjusting the noise index based on the nominal value.

5. A method in accordance with claim 1 further comprising determining, by the processor, a function of a projection area from a scout scan of a patient, wherein said adjusting a noise index comprises adjusting the noise index based on the function of the projection area.

6. A method in accordance with claim 1 further comprising:
receiving, by the processor, a patient size compensation based on a desired effect of the patient size on the noise index;
receiving, by the processor, a nominal value of a function of a first projection area, the nominal value calculated from an average size of parts of a plurality of patients;
receiving, by the processor, function of a second projection area obtained from a scout scan of a patient;
determining, by the processor, a noise adjustment from the patient size compensation, the nominal value calculated from the average size, and the function of the second projection area obtained from the scout scan;
receiving, by the processor, a nominal value of the noise index corresponding to an average size of patients, wherein said adjusting the noise index comprises changing the nominal value of the noise index based on the noise adjustment and the nominal value of the noise index.

7. A method in accordance with claim 1 further comprising:
generating an adjusted noise index at a z-axis location along a patient by adjusting the noise index;
generating other adjusted noise indexes at other z-axis locations along the patient;
generating an average noise index by averaging the adjusted noise index and the other adjusted noise indexes; and
applying x-rays to the patient based on the average noise index.

8. A method in accordance with claim 1 further comprising:
generating an adjusted noise index for scanning a first patient by adjusting the noise index;
generating additional adjusted noise indexes for scanning other patients by adjusting additional noise indexes;
storing a first correspondence between the adjusted noise index and a first electrical potential to be applied to an energy source;
storing a second correspondence between the additional adjusted noise indexes and a plurality of other electrical potentials to be applied to the energy source;
accessing, by the processor, one of the first electrical potential and the other electrical potentials, upon receiving a size of a second patient different than the first patient; and
applying the one of the first electrical potential and a second electrical potential from the other electrical potentials to an x-ray source.

9. A method for adjusting noise in an imaging system, said method comprising:
adjusting, by a processor, a noise within an image based on a patient size;
receiving, by the processor, a patient size compensation based on a desired effect of the patient size on the noise;
receiving, by the processor, a nominal value of a function of a first projection area, the nominal value calculated from an average size of parts of a plurality of patients;
receiving, by the processor, function of a second projection area obtained from a scout scan of a patient; and
determining, by the processor, a noise adjustment from the patient size compensation, the nominal value, and the function of the second projection area obtained from the scout scan, wherein said adjusting the noise comprises changing the noise based on the noise adjustment.

10. A medical imaging system comprising:
a source configured to generate radiation incident upon a patient;
a detector configured to detect the radiation; and
a processor configured to adjust a noise index within an image based on a patient size of the patient and a desired effect of a change in the patient size on a change in the noise index.

11. A medical imaging system in accordance with claim 10 wherein said processor is further configured to adjust parameters of a filter based on a projection area generated from a patient having the patient size.

12. A medical imaging system in accordance with claim 10 wherein said processor is further configured to:
receive, from a user, the patient size as an input; and
output the noise index based on the patient size.

13. A medical imaging system in accordance with claim 10 wherein said processor is further configured to:
determine an average size of parts of a plurality of patients; and
determine a nominal value of a function of a projection area from the average size, wherein said processor is configured to adjust the noise index based on the nominal value of the function.

14. A computer configured to adjust a noise index within an image based on a patient size and a desired effect of a change in the patient size on a change in the noise index.

15. A computer in accordance with claim 14 further configured to adjust parameters of a filter based on a projection area generated from a patient having the patient size.

16. A computer in accordance with claim 14 further configured to:
  receive, from a user, the patient size as an input; and
  output the noise index based on the patient size.

* * * * *